United States Patent [19]

Hart

[11] Patent Number: 4,687,636
[45] Date of Patent: Aug. 18, 1987

[54] SEPARATIVE SCINTILLATION PROXIMITY ASSAY

[76] Inventor: Hiram Hart, 3450 Wayne Ave., Bronx, N.Y. 10467

[21] Appl. No.: 567,687

[22] Filed: Jan. 3, 1984

[51] Int. Cl.⁴ .................. G01N 21/63; G01N 9/30; G01N 33/537
[52] U.S. Cl. .................. 422/57; 422/58; 422/69; 422/72; 436/537; 436/538; 436/807; 436/824
[58] Field of Search .............. 422/102, 57, 58, 68, 422/69, 72; 436/531, 539, 537, 558, 541, 807, 824

[56] References Cited

U.S. PATENT DOCUMENTS 4,286,637  9/1981  Wilson ........................... 422/57
4,558,014 12/1985  Hirschfeld et al. ............. 422/57

Primary Examiner—Christine M. Nucker
Attorney, Agent, or Firm—Stoll, Wilkie, Previto & Hoffman

[57] ABSTRACT

This invention relates to the use of differential separative properties and modified assay containers in improving the convenience of separative scintillation proximity assay (SSPA) and extending its range of practical application.

2 Claims, 8 Drawing Figures

SEPARATIVE SCINTILLATION PROXIMITY ASSAY

SUMMARY OF THE INVENTION

This invention relates to the use of differential separative properties and specialized transparent incubation and counting vials in appropriately isolating the scintillation causing elements being measured in order to improve the convenience and extend the range of applicability of SSPA.

BACKGROUND OF THE INVENTION

In scintillation proximity assay (U.S. Pat. No. 4,271,139) samples are customarily counted in standard scintillation vials after incubation. This is effective and reliable as an assay of non-optically absorbing media. For most unprocessed biological fluids, however, the count rates can be significantly reduced by optical absorption. One ml. of otherwise non-interactive serum added to a clear 10 ml of sample in a 22 ml scintillation vial can easily reduce the measured counts by as much as 40%. Two ml of serum so introduced can result in a count rate reduction of as much as 70%. The direct utilization of undiluted serum for SSPA testing is therefore likely to be unrealistic since the optical absorption of signal photons emitted randomly throughout the sample volume is predictably too large for internal standardization to be reliable.

To reduce the effect of optical absorption it has been found desirable to so localize the signal emitting dimers within a portion of the sample chamber that the signal path length to the detector (s) and, therefore, the optical absorption is minimized. This localization can be accomplished of course, by a variety of methods reflecting whatever differences in size, density, electrical, magnetic, and chemical properties exist or are created among the interacting particulate elements.* A typical additional embodiment makes use of selective filtration in which large particles are retained and unbound small particles pass through. The filter itself can then either be assayed in situ or following removal.

*The examples appended make use of centrifugation techniques to effect localization.

A related adaptation of SSPA has been found to be effective in detecting the pressure of and evaluating the susceptibility of infectious organisms.

Other and further objects of the present invention will become apparent upon an understanding of the illustrative embodiments about to be described or will be indicated in the appended claims, and various advantages not referred to herein will occur to one skilled in the art upon employment of the invention in practice.

BRIEF DESCRIPTION OF THE DRAWINGS

The operation of the assay systems and benefits that may be derived from the invention may be better understood through reference to the following description of embodiments and FIGS. 1-8.

DESCRIPTION OF THE PREFERRED EMBODIMENTS

Figure 1:
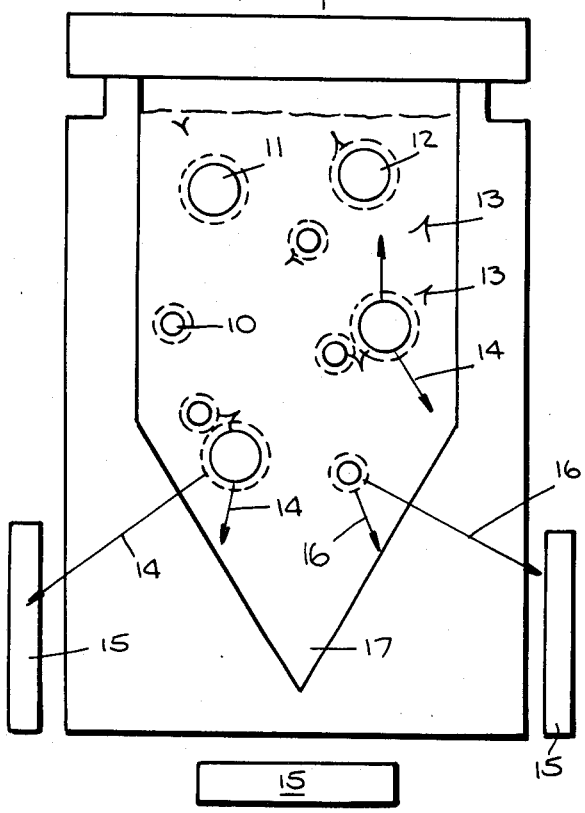
Figure 2:
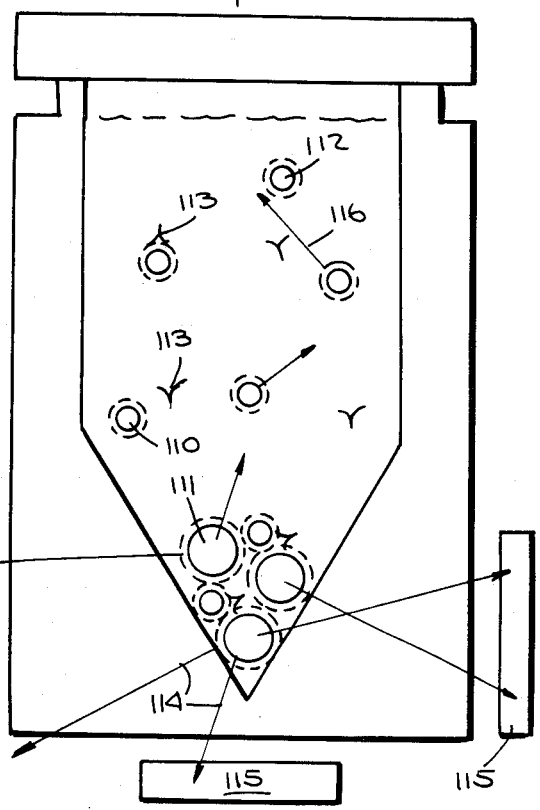

In the accompanying FIGS. 1 and 2, latex particles either labelled with tritium or another relatively short range beta emitter such as 14-C or 35-S10 and 110 significantly larger (or denser) scintillant latex particles 11 and 111 are represented before and after centrifugation. The antigen or antibody coatings 12 and 112 and the reactant under assay 13 and 113 are also represented before and after centrifugation. The arrows 14 and 114 represent photons produced in the scintillation particles by radiation from the attached radioactive particles. Photons whose paths terminate within the medium or do not otherwise arrive at the detectors 15 or 115 will of course not be recorded. The arrows 16 and 116 represent background photons arising from the residual fluorescence still present even in the Tinuvin P doped polystyrene particles described in U.S. Pat. No. 4,388,296. The arrows 17 and 117 represent the bottom region of the counting vial.

Since the radioactive latex particles are much smaller than the scintillant latex particles a higher speed of centrifugation is required to spin down those radioactive particles which are freely suspended in the medium than the larger scintillant particles. If, after appropriate incubation, the counting vial is centrifuged at a speed sufficient to spin down the scintillant particles but insufficient to spin down the freely suspended radioactive particles, it follows that essentially only those radioactive particles which are bound to scintillant particles will be concentrated in region 117. Measurement of the photons arriving at the detectors 115 from the restricted region 117 results in several improvements in SSPA.

First of all since the signal producing dimers are now localized within the relatively small region 117, the system detectors can be grouped around this region maximizing the geometric efficiency of signal detection. Secondly, the effect of optical absorption within the medium is grossly reduced because the photon paths from the signal producing elements to the detectors are now principally through the transparent glass or plastic of the scintillation vials. Finally, background photon counts from self-activated radioactive particles are now almost completely suppressed by the fact that the unbound radioactive particles remain suspended at relatively large distances from the detectors and by the fact that their photon path lengths toward the detectors continue to include the optically absorbing sample medium. Background counts could, of course, be even further reduced by adding an absorbing soluble dye to the medium. Alternatively, of course, the scintillant particles can be the small particulates and the radioactive particles the larger or denser ones. The diameter of the scintillant particles should, however, be at least as large as the mean free path of the activating radiation to ensure effective photon production.

Figure 3:
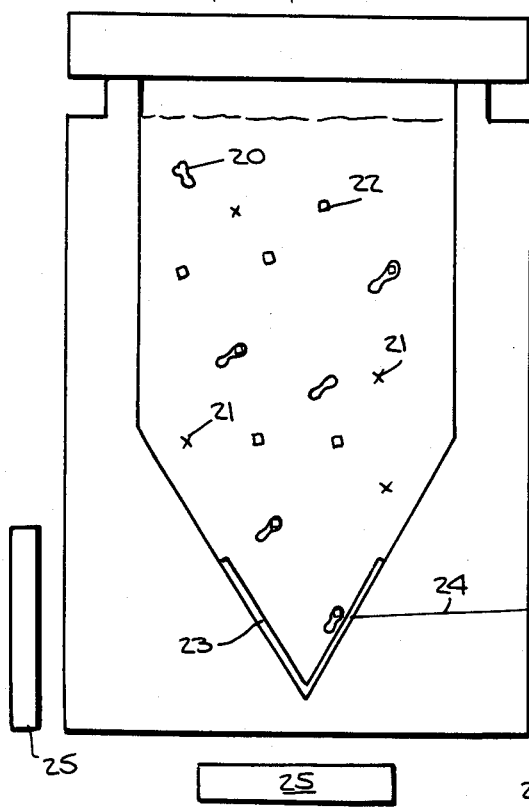
Figure 4:
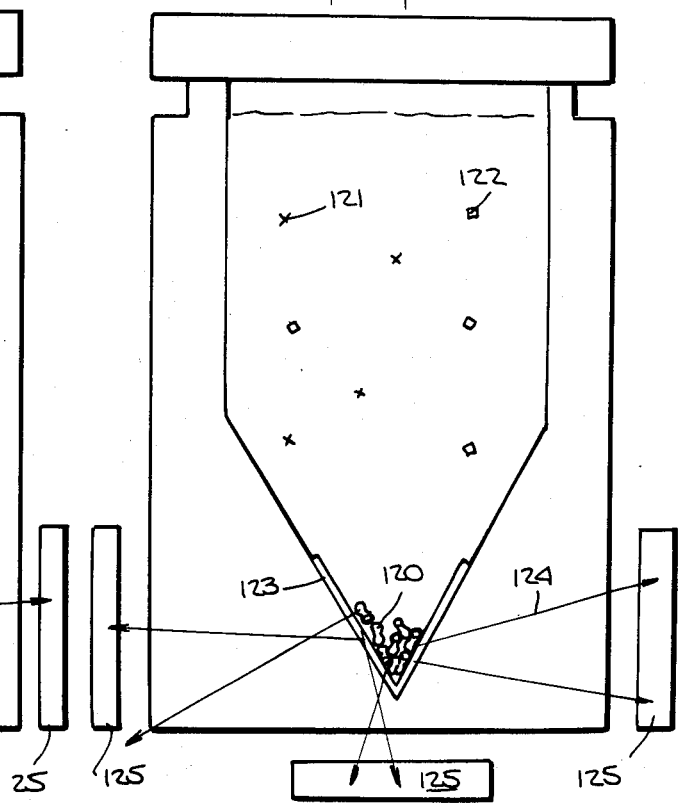

In the accompanying FIGS. 3 and 4, elements 20 and 120 represent either known or unknown organisms whose susceptibility to a known agent 21 and 121 is being examined. Elements 22 and 122 represent a radioactively labelled common nutrient such as $C^{14}$ glycine or a nucleic acid constituent which is normally incorporated during metabolism by the class or organisms being studied. The elements 23 and 123 represent a coating which emits scintillation flashes 24 and 124 upon excitation by the relatively short range beta rays from the radioactive $C^{14}$ atoms of the labelled nutrient. The flashes are in turn recorded by the detectors 25 and 125.

Following suitable incubation the sample is centrifuged under conditions chosen to selectively spin down any of the class of organisms under consideration while leaving the low molecular weight nutrient in solution. As can be seen in FIG. 4, activation of the scintillant coatings 123 by the beta radiation from $C^{14}$ incorporated in the growing organism results in signal photons arriving at the detectors 125.

The assay is extremely sensitive since only a small amount of $C^{14}$ incorporated into relatively few growing organisms can give rise to a significant signal. The background is small because the average range of the $C^{14}$ beta rays is only ~10 microns and therefore essentially only the $C^{14}$ incorporated in the surface spun down organisms gives rise to scintillations. In view of the much higher specific activity of $S^{35}$, the method can be made even more sensitive by using appropriate sulphur 35 labelled compounds.

Assessment of the efficacy of various anti biotics in considering the treatment of a septicemia of initially unknown etiology should be possible, usually in less than 8 hours. A relatively large and progressively increasing signal suggests of course that growth is not inhibited and the antibiotic being tested would probably be ineffective in vivo. A relatively constant low level of counts would suggest conversely that growth of the organism has been inhibited by the agent being tested.

The method outlined in connection with FIGS. 3 and 4 can be easily adopted for simultaneous testing of several agents for their effectiveness in inhibiting the growth of an infectious organism.

Figure 5:
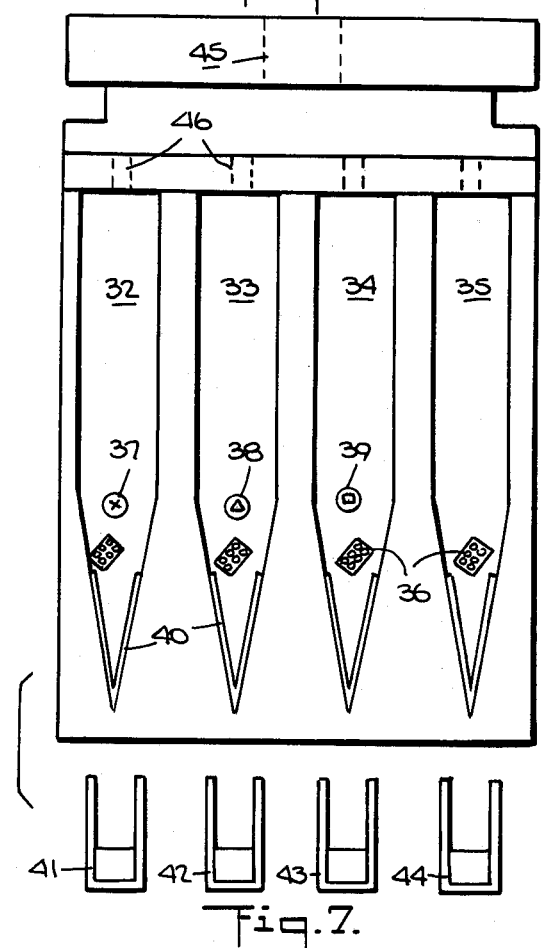

The multichambered vial 31 of FIG. 5 is initially evacuated. Each of the chambers 32, 33, 34 and 35 can contain one or more growth media of choice incorporating a $C^{14}$ or $S^{35}$ labelled nutrient 36 as well as the different growth inhibitors being rested 37, 38 and 39. For longer shelf-life it may be desirable for the growth media and growth inhibitors to be in solid but soluble form. The bottom of each chamber has a fluorescent coating 40, which may be plastic impregnated with a fluorescent compound such as DPF and a wave length shifter such as bis. MSB. A series of collimated scintillating detectors 41, 42, 43 and 44 with each of their fields of view restricted to a single chamber serve as the detection system. The detectors may be discrete as represented or for compactness may actually be a single appropriately segmented microchannel plate with associated circuitry.

In operation the biological fluid sample diluted possibly with ~25% isotonic saline is introduced under sterile conditions through the rubber closure 45. The sample fluid is drawn by the vacuum into each of the chambers 32, 33, 34 and 35 through the capillary apertures 46. The vial should be gently shaken during filling to promote intrachamber mixing. The vial should be kept reasonably upright to minimize interchamber fluid transfer by backflow through the capillaries. The capillaries can also be convoluted or have porous plugs to reduce such backflow.

Figure 6:
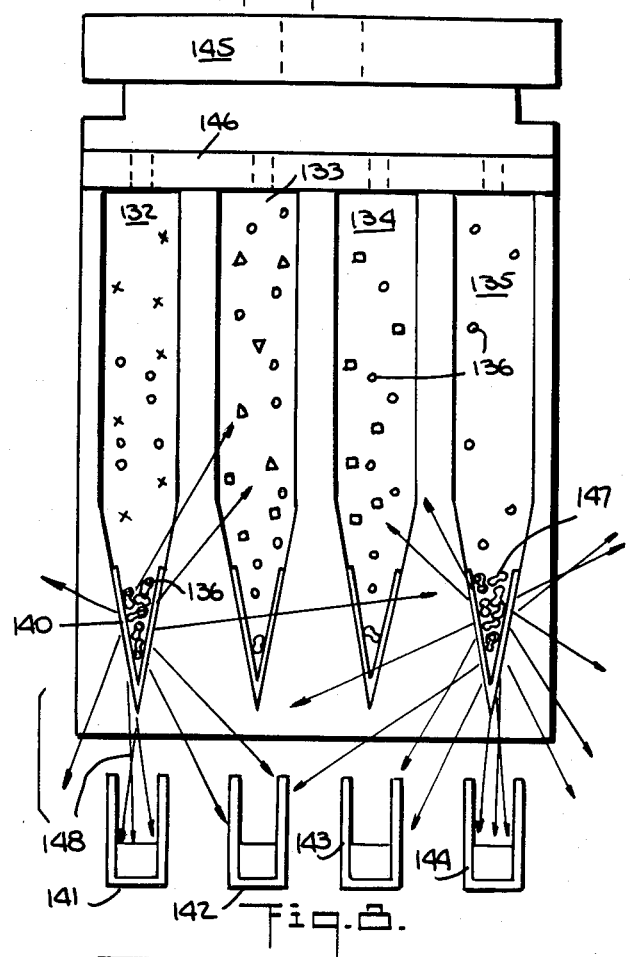

After incubation the vial is centrifuged to spin down the organisms 147 with the result diagrammed in FIG. 6. Since the density of most cellular organisms is not too different from that of sera, dilution of the sample with ~25% isotonic saline serves to ensure that the organisms will in fact be spun down rapidly. In those chambers 133 and 134 in which no growth or minimal growth and/or nuclear acid synehesis occurs, little if any extra radioactive labelled nutrient 136 will be brought in close proximity to the scintillant coating 140. The detectors 142 and 143 monitoring these chambers should therefore record close to background levels. In chamber 132 and the control chamber 135 in which cellular growth does occur, much more of the radioactively labelled nutrient 136 will be brought into close proximity to the scintillant coating and the detectors 141 and 144 should record an elevated rate of incident photons 148. Instead of using a scintillant coating, scintillant particles can be used which have a range of sedimentation rates comparable to that of the class of organisms being considered. During centrifugation the scintillant particles and labelled organisms will be coprecipitated resulting in a SSPA signal.

The above technique may be compared with current methods in which assays of $C^{14}O_2$ arising from the whole serum sample following incubation with $C^{14}$ labelled glucose are used just to test for the presence of growth. A separate subculturing procedure is then required to select the medication of choice. Since the present method usually takes over 2 days and the new technique should not require more than a few hours, SSPA is approximately 5-10 times faster.

Fluorescent compounds which are either bound to the surface of or incorporated within growing organisms can be substituted for radioactive nutrients in labelling the organisms. Laser beam activation of the sediment following centrifugation would then give rise to the desired signal. The method is described in detail in the discussion of FIGS. 7 and 8 below.

Figure 7:
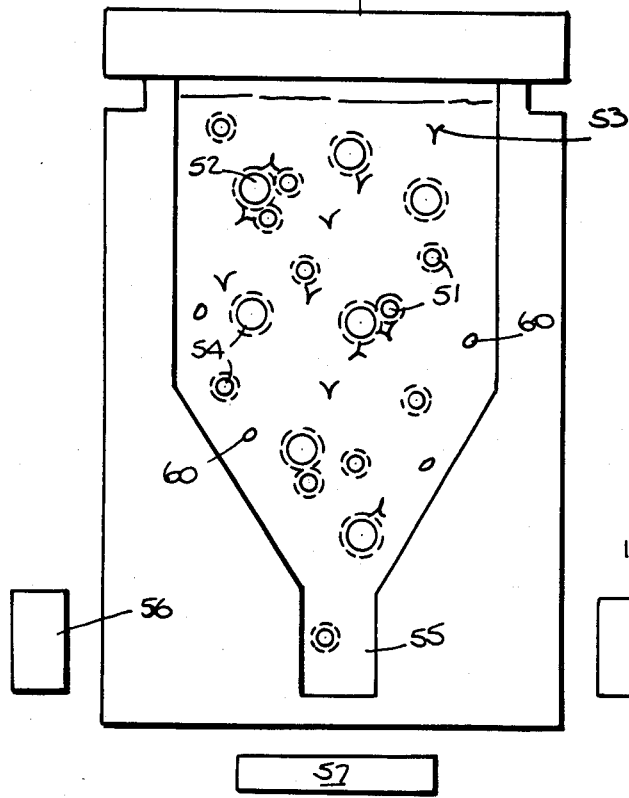
Figure 8:
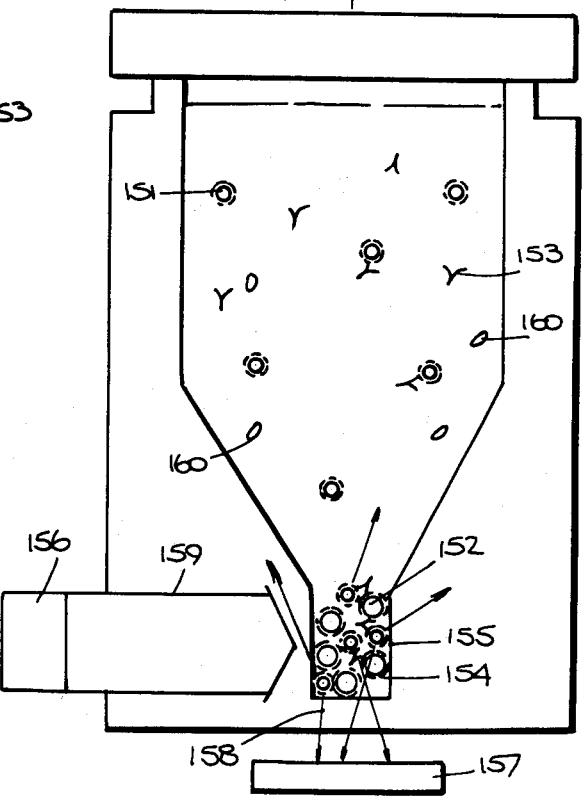

A final modified incubation scintillation vial counting system is diagrammed in FIGS. 7 and 8. Elements 51 and 151 represent small fluorescent latex particles and elements 52 and 152 represent large optically inert latex particles before and after centrifugation. Elements 53 and 153 represent antibody or antigen molecules having a binding affinity for the latex particle coatings 54 and 154. Elements 55 and 155 represent the sub-chamber of the vial which is to be irradiated. Elements 56 and 156 represent a laser emitting a beam of wave length $\lambda_1$. Elements 57 and 157 represent detectors which have been so filtered or otherwise selected that they do not respond to radiation of wave length $\sim\lambda_1$, but they will respond to wave lengths in the band about $\lambda_2 > \lambda_1$ where $\lambda_2$ corresponds to major fluorescence radiation of the fluorescent particles 51 and 151 when they are excited by radiation of wave length $\lambda_1$. Elements 60 and 160 represent a soluble non-binding dye which absorbs radiation in both the $\lambda_1$ and $\lambda_2$ regions. The dye serves to suppress the background signal arising from any laser beam or other stray irradiation of the freely suspended fluorescent latex particles following centrifugation.

After incubation and subsequent centrifugation at speeds suitable for spinning down the larger latex particles but leaving the smaller unbound fluorescent latex particles still suspended throughout the medium, those fluorescent particles bound to the larger latex particles will be concentrated in the sub-chamber of the vial 155. The laser beam element 159, of wave length $\lambda_1$ from element 156 now activates the bound fluorescent particles which emit fluorescence radiation over a band of wave lengths about $\lambda_2 > \lambda_1$. The optical detector 157 measures the amount of incident photons 158 in the band of wave lengths $\lambda_2$ arriving from the sub-chamber 155. This signal is correlative to the amount of fluorescent particles in the sub-chamber which is in turn correlative to the available amount of antibody, antigen or other interparticulate binding elements in the medium.

This external laser excitation form of SSPA while similar to prior examples does not, of course, require the use of radiosotopes.

As mentioned briefly above, the laser excitation mode of SSPA is also applicable to the detection of growing organisms. Fluorescent elements which are either bound to or incorporated in the growing organism can be present in the medium. Following centrifugation, the sediment would be subject to laser beam excitation and the fluorescence detected as before.

A broad laser beam is diagrammed in FIG. 8 corresponding to the large amount of sediment indicated for ease of illustration. In actual application usually only a thin layer of sediment will be present on the bottom of the sub-chamber. The laser beam should be restricted to this thin layer as far as possible. By restricting the laser beam as far as possible to the actual sediment unbound fluorescent material still suspended in the medium will not be significantly activated, thus tending to optimize the signal to noise ratio. A convenient method of irradiating the bottom precipitate layer is to direct the laser beam from below making an angle of $\lesssim 45°$ with respect to the normal. The reflected light will miss the detector 157, and the refracted beam should be rapidly attenuated by the absorbing dye molecules 160.

As various changes may be made in the form, construction and arrangement of the parts herein without departing from the spirit and scope of the invention and without sacrificing any of its advantages, it is to be understood that all matter herein is to be interpreted as illustrative and not in a limiting sense.

EXAMPLE I

Separative SPA (SSPA) with Different Size LH and L* Particles

I.

Preparation of Particles (a) Tritiated Particles

A suspension of 400 mgm of 0.455$\mu$ diameter surface carboxylated latex particles (Dow Diagnostics-Seragen) in 4 ml of $H_2O$ was labelled at New England Nuclear by Welsbach tritiation—specific activity $\sim 0.250$ mc$_i$ $^3H$/mgm particles and returned as a suspension in 10 ml $H_2O$. An aliquot of 40 mgm of the particles in 1 ml $H_2O$ was impregnated with Tinuvin P as described in Hart (U.S. Pat. No. 4,388,296). Designated as LH particles.

(b) An aliquot of surface carboxylated 1.1$\mu$ diam latex particles (Serogen) in $H_2O$ was impregnated with DPF and bis MSB as described in Hart (U.S. Pat. No. 4,388,296). Designated as L* particles.

II.

Preparation of Solutions (a) Buffer Solutions

The concentrated phosphate buffer is as described in Hart (U.S. Pat. No. 4,382,074).

Sol. A: 3.2 gms $NaH_2PO_4.H_2O$/100 ml $H_2O$
Sol. B: 5.3 gms $Na_2HPO_47H_2O$/100 ml $H_2O$
Concentrated Buffer: 16 ml Sol A + 84 ml Sol. B.
Stock Phosphate Buffer: 1 part Conc. Buffer + 3 parts $H_2O$ adjusted to pH 8.0 with NaOH.

(b) Solution C is prepared by dissolving 100 mgm of Rabbit albumin (Pentex; Miles Laboratories) in 100 ml of a 0.005% Thimerosal solution containing 95 ml of 0.9% NaCl in $H_2O$ + 5 ml of stock phosphate buffer pH $\sim 8.0$. Higher concentrations of Rabbit albumin ($\sim$1-2%) can be used to further suppress non-specific interparticulate binding (i.e. background counts) in high sensitivity applications.

III.

Surface Bonding of Human Albumin to the Two Sets of Particles (LH and L*)

(a) Bonding to LH particles

To a suspension of $\sim 3$ mgm of LH particles in 2 ml $H_2O$ slowly add a freshly prepared solution of $\sim 3$ mgm CBDD (1-Ethyl-3(3-Dimethylamino-propyl)-Carbodiimide Hydrochloride; Pierce No. 22980) in 1.0 ml $H_2O$ (pH $\sim 8.0$) over a period of 10 minutes while gently shaking.

Then slowly add a freshly prepared solution of $\sim 3$ mgm crystalized human albumin (Pentex, Miles Lab.) in 1 ml $H_2O$ to the suspension over an additional period of 10 minutes while gently shaking.

Store overnight at 4° C.
Wash particles 4 times.
Particles resuspended in 4 ml solution C.
Ready for use (Designated as HALH particles).

(b) Binding to L* particles

Same as III a. except that $\sim 10$ mgm of the larger L* particles are used as compared to only $\sim 3$ mgm of the smaller LH particles. (Designated as HAL* particles).

IV.

Rabbit Anti-Human Albumin Antibody SSPA (a) Prepare 6 conically bottomed scintillation vial inserts ("SMAC" vials; Technicon—with the midline circular lip ground off) containing 3.6; 3.5; 3.4; 3.2; 2.8, 2.0 and 0.0 ml of Sol. C and raise the fluid volume in each vial to 3.6 ml of adding rabbit serum.

(b) Prepare a suspension of 0.2 mgm of HALH particles and 0.6 mgm HAL* particles in 2.0 ml of Sol. C. Designates as suspension IV b. For higher sensitivity applications do not pre-mix the particles but rather add them separately in step d. to the samples being assayed. This tends again to reduce non-specific interparticulate binding which can occur when relatively high concentration suspensions are stored for any length of time.

(c) Dissolve 4 mgm of Rabbit Anti-Human Albumin Antiserum (GIBCO) in 2 ml Sol. C. Designate as Solution IV C.

(d) Add 0.2 ml of suspension IVb. to each vial and mix.

(e) Add 0.2 ml of solution IVC. to each vial and mix. A titer of $10^{-3}$ of rabbit antihuman albumin antiserum is now present in each vial.

Incubate at 37° for 1 hour.

(f) Count each sample for two minutes on a liquid scintillation counter gated for $^3H$ and then centrifuge at 2500 rpm (1740 g) for 5 minutes at 4° C. Such centrifugation is effective in precipitating the 1.1$\mu$ particles but less effective in precipitating unbound 0.455$\mu$ particles.

(g) Count each sample again for two minutes on the liquid scintillation counter. The resulting counts appear in Table 1.

TABLE 1

| Vial Insert | Distributed | Separated (centrifuged) | Proportionate Sensitivity Following Centrifugation |
|---|---|---|---|
| 0.0 ml added Rabbit Serum | 58,166 | 93,860 | 1.61 |
| 0.1 ml R.S. | 33,728 | 76,105 | 2.26 |
| 0.2 ml R.S. | 26,090 | 61,495 | 2.36 |
| 0.4 ml R.S. | 16,966 | 49,835 | 2.94 |
| 0.8 ml R.S. | 7,147 | 35,215 | 4.93 |
| 1.6 ml R.S. | 2,045 | 20,915 | 10.23 |

TABLE 1-continued

| Vial Insert | Distributed | Separated (centrifuged) | Proportionate Sensitivity Following Centrifugation |
|---|---|---|---|
| 3.6 ml R.S. | 354 | 9,485 | 26.79 |

The separated (centrifuged) samples not only provide a larger signal but they exhibit much less dependence upon the optical absorption of the rabbit serum. This indicates that, when necessary, larger serum samples can now be more efficiently utilized and the effect of variations in the optical properties of individual patient sera should be much less important. The bottom of the "SMAC" vials used is a ~3/16" circular disk which can result in comparable path lengths through the absorbing fluid medium. A substantial further reduction in optical absorption may therefore be expected with vials having pointed conical bottoms as diagrammed in FIGS. 1 and 2.

Similar results are obtained when the variable amounts of rabbit serum added to the vials are replaced by corresponding amounts of a saturated solution of the inert dye bromophenol blue.

EXAMPLE 2

SSPA with Metabolically Induced Radioactively Labelled Organism

I.

Preparation of the Fluorescent Coating in FIGS. 3 and 4

(a) Preparation of Scintillant Plastic

Place ~1 gm. of Lucite in a closed glass vial containing a solution of 36 mgm DPF+6 mgm Bis MSB in 10 ml benzene. Heat to 50° C. for ~12 hours. The Lucite should be completely dissolved. Designate as scintillant plastic solution SPS.

(b) Coating Formation

Carefully place ~0.2 ml of SPS in bottom of each plastic scintillation vial insert. The vial insert may be flat bottomed. Leave uncovered for ~12 hours at ~50° C. The benzene should evaporate leaving behind a fluorescent layer of plastic on the bottom. For inserts with a conical bottom the plastic insert can be slowly rotated about its cylindrical axis appropriately tilted during the evaporation. In general the coating will be more adherent if a plastic vial is used which is at least slightly soluble in benzene.

II.

Sample Preparation (a) Medium Used

Place 4 ml of a 20% solution of sterile rabbit serum in $H_2O$ (serum filtered through a 0.45$\mu$ Gelman filter) containing 0.07$\mu$ C $C^{14}$ glycine into each of 6 scintillant plastic coated inserts.

(b) Inoculum

Inoculate each of the samples such that concentrations of viable e. coli (Difco ATCC #25922) in the samples prior to incubation range from 0 to $5 \times 10^5$/ml.

(c) Results

Table 2 indicates the count rates obtained with a standard liquid scintillation counter energy gated for $C^{14}$ after incubation of the samples at 37° C. and 10 minutes of centrifugation at 2500 rpm (1740 g).

TABLE 2

| Sample Preparation | Initial Concentration of e. coli | | | | | |
|---|---|---|---|---|---|---|
| | $5 \times 10^5$ ml | $5 \times 10^4$ ml | $5 \times 10^3$ ml | $5 \times 10^2$ ml | 50/ml | 0 |
| Initial Cts./min. | 179 | 141 | 178 | 145 | 173 | 123 |
| 8 hours of Incub. + 10 min. cent. | 7139 | 2297 | 711 | 265 | 274 | 274 |
| 20 hours of Incub. + 10 min. cent. | 14,888 | 19,361 | 19,345 | 13,916 | 2300 | 286 |

The vials counted after 8 hours were removed from the liquid scintillation counter, gently agitated to resuspend the e coli and placed back in the incubator for another 12 hours.

Note that a clearly elevated count rate occurs with an inoculation of 5000 e. coli/ml within eight hours.

When the experiment is repeated with media containing therapeutic levels of an anti-biotic such as tetracycline no increase in counts occurs following incubation suggesting that growth has been suppressed.

The reduced 20 hour count rate of the sample having the highest initial concentration ($5 \times 10^5$/ml) is perhaps related to nutrient depletion or waste accumulation in the medium limiting the average number of cell divisions per initial viable cell. As a result, for the $5 \times 10^5$/ml sample more of each e coli cell mass is probably on the average derived from unlabelled nutrients.

EXAMPLE 3

External Excitation SSPA

Measurement of fluorescence excitation spectra against a background of incident radiation is easily carried out and a wide range of fluorescent compounds and experimental arrangements exist (I. Berlman Fluorescence Spectra of Aromatic Molecules 2nd Edition. Academic Press 1971). For routine stable incorporation of a compound in latex particles without the additional use of sealants etc. the compound should be reasonably soluble in organic solvents and highly insoluble in water. The compound should exhibit a high excitation cross-section and quantum yield and a substantial fluorescence wave-length shift. The choice of the laser and the related selection of the fluorescent compound is principally one of cost and convenience since literally thousands of combinations are possible.

Simply to demonstrate that the method outlined in FIGS. 7 and 8 is feasible and practical without attempting to optimize the assay procedure at all a pilot system was developed based upon the popular inexpensive and reliable Spectra-Physics Number 155½ mw helium-neon laser (Edmund Scientific). For helium-neon lasers, the available compounds are somewhat restricted since most of the excitable dye in the 632.8 nm wave length region such as nile blue and carbazine tend to be water soluble. A relatively water insoluble fluorescent dye oxazine 725 (Exciton Co.) did prove to be usable however.

I.

Incorporation of Oxazine 725 in Latex Particles (a) Dissolve 5 mgm Oxazine 725 in 1.0 ml $CH_2Cl_2$. Designate as DS.

(b) Add ~0.05 ml of DS into 2 ml of $H_2O$ containing enough Tween so that upon sonicating an emulsion is formed without a separate $CH_2Cl_2$ phase.

(c) Add surface carboylated 0.455μ latex particles (~15 mgm in 2 ml H₂O) drop by drop while Ib. is sonicating.

(d) Vacuum evaporate (e) Resuspend in H₂O, sonicate, and wash 3×. Designate the 0.455μ particles as L*.

II.

Surface Bonding of Human Albumin to Both Sets of Particles

The procedure is carried out exactly as in Section III of example 1 except that:

a. The fluorescent 0.455μ diameter particles (L*) are now the signal producing components of the laser excited particulate dimers and following coating with human albumin are designated as HAL*.

b. Since the human albumin coated 1.1μ particles are now neither radioactively labelled nor scintillating, they are designated as HAL.

III.

Optical System a. Incident Beam

The exciting radiation was a ½ mw Spectra-Physics Helium-Neon laser beam filtered by a 632.8 nm narrow band pass interference filter (e.g. Ealing Catalog No. 35-3912). Alternatively one or more short pass filters could have been used (Ealing Catalog Nos. 35-5404 or 35-5420). A simple double concave lens was used as a beam expander so that the cross-section of the beam incident on the vial bottom was ~½ the cross-section of the bottom of the vial.

b. Fluorescence Detection

The detector consisted of a filter (6 mm of Schott Catalog No. RG 645 color filter glass) and a cadmium selenide photo-conductive cell (Clairex Catalog No. CL5M4) connected to a 0-150 volt d.c. power supply. Alternatively one or more long pass filters could have been used (Ealing Catalog No. 35-5669). The current output was determined with a microammeter.

IV.

Sample preparation and results

Eight fairly flat bottom vials (Fisher 03-339-15A) were used.

Four ml of Sol. C saturated with Bromophenol Blue and containing a mixed suspension of the HAL and HAL* particles [0.3 mgm HAL+0.1 mgm HAL* per vial] were placed in each vial. The titers of rabbit antisera to human albumin in 7 of the eight vials were: $10^{-2}$, $10^{-3}$, $10^{-4}$, $10^{-5}$, $10^{-6}$, $10^{-7}$, $10^{-8}$ with the eighth vial containing no antiserum and serving as a control.

The vial were incubated for 1 hour at 37° C. The vials were then centrifuged at 1400 rpm (550 g) for ~15 minutes. The laser beam was then directed from below at an angle of ~45° to the precipitate layer (~45° to the normal to the preciptate layer) with the results indicated in Table 3.

TABLE 3

| Photoconductive Current at 100 volts for Different Titers | | |
|---|---|---|
| Sample | Titer | Reading(s) μa. |
| 1# | $10^{-2}$ | 4.33 |
| 2# | $10^{-3}$ | 3.33 |
| 3# | $10^{-4}$ | 1.10 |
| 4# | $10^{-5}$ | 0.63 |
| 5# | $10^{-6}$ | 0.36 |
| 6# | $10^{-7}$ | 0.29 |
| 7# | $10^{-8}$ | 0.30 |
|  |  | 0.28 |
| 8# | Control | 0.28 |

It should be noted that the tabulated results were obtained with a physical and biochemical system which was by no means optimal. It may be anticipated that with flatter bottomed vials and more effective dye laser-combinations, a substantial increase in sensitivity and accuracy can be achieved. The background (i.e. control) value, if indicated, can also be reduced with a higher concentration of Rabbit Albumin or other surfactant.

Having thus described my invention, I claim:

1. A centrifugal unit of use in a plurality of scintillation proximity assay of biological materials consisting essentially of a top portion, body portion, and bottom portion, said top portion having a unitary hollow space adapted to receive a separably engaged cover providing fluid access to said hollow portion, said body portion having a plurality of hollow elongated sections each of which terminates in a portion of restricted volume circumscribed by a surface of a transparent section of said bottom portion, each of said hollow elongated sections having fluid communication with said hollow top portion, all said circumscribed surfaces provided with a fluorescent coating adapted to be activated by radiation to give a detectable light pulse correlative to said biological material in each of said hollow sections.

2. The centrifugal unit of claim 1 wherein said circumscribed surface is uniformly smooth to within several microns so that on processing a relatively even layer of precipitate of said biological material is deposited.

* * * * *